United States Patent [19]

Nakatsuka et al.

[11] Patent Number: 4,883,876
[45] Date of Patent: Nov. 28, 1989

[54] ACYLATED VINCAMINIC ACID DERIVATIVES

[75] Inventors: Shin-ichi Nakatsuka, Aichi; Masatoshi Hayashi, Saitama; Sadakazu Yokomori, Urawa; Yoshimoto Nakashima, Ageo; Katsuo Hatayama, Omiya; Hiroaki Araki, Hasuda, all of Japan

[73] Assignee: Taisho Pharmaceutical Co., Ltd., Japan

[21] Appl. No.: 239,687

[22] Filed: Sep. 2, 1988

[30] Foreign Application Priority Data

Sep. 7, 1987 [JP] Japan .................................. 62-223753

[51] Int. Cl.$^4$ .................. C07D 461/00; A61K 31/475
[52] U.S. Cl. .................................................... 546/51
[58] Field of Search ........................... 514/283; 546/51

[56] References Cited

U.S. PATENT DOCUMENTS 4,001,251  1/1977  Najer et al. ............................ 546/51
4,146,643  3/1979  Pfäffli .................................. 514/283

FOREIGN PATENT DOCUMENTS 2703920  8/1977  Fed. Rep. of Germany ........ 546/51

OTHER PUBLICATIONS

Lewin et al., Heterocycles, vol. 14, No. 12, pp. 1915–1920 (1980).

Primary Examiner—Mukund J. Shah
Assistant Examiner—Diana G. Rivers
Attorney, Agent, or Firm—Lorusso & Loud

[57] ABSTRACT

Vincaminic acid derivatives represented by the formula

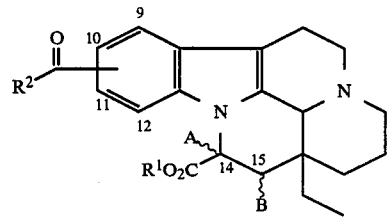

wherein $R^1$ is a hydrogen atom, an alkyl group having 1 to 8 carbon atoms or an alkoxyalkyl group having 2 to 6 carbon atoms, $R^2$ is a hydrogen atom, an alkyl group having 1 to 10 carbon atoms, a halogenated alkyl group having 1 to 5 carbon atoms, a cycloalkyl group having 3 to 6 carbon atoms, an alkoxycarbonylallyl group having 3 to 8 carbon atoms, an alkenyl group having 2 to 4 carbon atoms, a phenyl group, a phenyl group substituted by alkoxy groups each having 1 or 2 carbon atoms or a thienyl group, A is a hydroxy group, B is a hydrogen atom, or A and B together form a valence bond, and the acid addition salts thereof are disclosed. These compound are useful as therapeutic effect on cerebovascular injuries.

2 Claims, No Drawings

ACYLATED VINCAMINIC ACID DERIVATIVES

BACKGROUND OF THE INVENTION

1. FIELD OF THE INVENTION

The present invention relates to vicaminic acid derivatives, and more particularly relates to vincaminic acid derivatives having the therapeutic effect on cerebovascular injuries.

2. DESCRIPTION OF THE PRIOR ART

There are already known some vincaminic acid derivatives having cerebral vasodilating effect, protective effect on cerebral ischemia, cerebral metabolic accelerating effect and the like (British Pat. Nos. 2,062,619A and 1,492,579A and European Pat. No. 170,926A).

However, the pharmacological effect of the prior art compounds is not sufficient, and there is a need for appearance of the vincaminic acid derivatives having improved cerebral vasodilating effect, protective effect on ischemia, and cerebral methabolic accelerating effect.

SUMMARY OF THE INVENTION

Under these conditions, the present inventors have found that the vicaminic acid derivatives in which an acyl group or a formyl group is introduced to the benzene ring of the eburnamenin skeleton show an improved effect on cerebovascular injuries, and accomplished the present invention.

An object of the present invention is to provide vincaminic acid derivatives represented by the formula

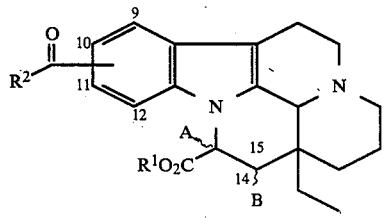

(I)

wherein $R^1$ is a hydrogen atom, an alkyl group having 1 to 8 carbon atoms or an alkoxyalkyl group having 2 to 6 carbon atoms, $R^2$ is a hydrogen atom, an alkyl group having 1 to 10 carbon atoms, a halogenated alkyl group having 1 to 5 carbon atoms, a cycloalkyl group having 3 to 6 carbon atoms, an alkoxycarbonylalkyl group having 3 to 8 carbon atoms, an alkenyl group having 2 to 4 carbon atoms, a phenyl group, a phenyl group substituted by alkoxy groups each having 1 or 2 carbon atoms or a thienyl group, A is a hydroxyl group, B is a hydrogen atom, or A and B together form a valence bond, and the acid addition salts thereof.

DETAILED DESCRIPTION OF THE INVENTION

In the present invention, the alkyl group having 1 to 8 carbon atoms for $R^1$ refers to a straight or branched chain alkyl group such as, for example, a methyl group, an ethyl group, a n-propyl group, an isopropyl group, a n-butyl group, a t-butyl group, a n-pentyl group, an isopentyl group, a n-hexyl group and the like.

The alkoxyalkyl group having 2 to 6 carbon atoms refers to those in which the alkoxy moiety has 1 to 4 carbon atoms, and the alkyl moiety has 1 or 2 carbon atoms such as, for example, a methoxymethyl group, an ethoxymethyl group, a n-propoxymethyl group, a methoxyethyl group, a t-butoxyethyl group and the like.

The alkyl group having 1 to 10 carbon atoms for $R^2$ refers to a straight or branched chain alkyl group such as, for example, the alkyl group described above, n-heptyl group, an isoheptyl group, a n-octyl group, a n-nonyl group, a n-decyl group and the like.

The halogenated alkyl group having 1 to 5 carbon atoms refers to a straight or branched chain alkyl group attached to a halogen atom at any available positions such as, for example, a chloromethyl group, a chloroethyl group, a bromoethyl group, a fluoroethyl group, a chloro-n-propyl group, a chloroisopropyl group, a bromo-n-propyl group, a chloro-n-butyl group, a bromo-n-butyl group, a bromoisobutyl group, a chloro-t-butyl group, a chloro-n-pentyl group and the like.

The alkoxycarbonylalkyl group having 3 to 8 carbon atoms refers to those which contain the alkoxy moiety having 1 to 4 carbon atoms (e.g., a methoxy group, an ethoxy group and the like), a carbonyl group and the alkyl moiety having 1 to 4 carbon atoms (e.g., a methyl group, an ethoxy group, a propyl group and the like). Examples of the group are an ethoxycarbonylmethyl group, a 2-methoxycarbonylethyl group, a 2-ethoxycarbonylethyl group, a 2-propoxycarbonylethyl group, a 3-ethoxycarbonylpropyl group and the like.

The alkenyl group having 2 to 4 carbon atoms refers to a straight or branched chain alkenyl group such as, for example, a vinyl group, a 1-propenyl group, a 2-propenyl group, a 1-butenyl group, a 3-butenyl group, a 2-methyl-1-propenyl group, a 2-methyl-2-propenyl group and the like.

The phenyl group substituted by the alkoxy groups each having 1 or 2 carbon atoms refers to the phenyl group substituted by 1 to 3 of the alkoxy group at any available positions.

The group $R^2CO-$ may occur at any available position of the benzene ring.

The acid addition salts of the compound of Formula I are the salts derived from any inorganic acids and organic acids. Examples of the acid are hydrochloric acid, hydrobromic acid, sulfuric acid, phosphoric acid, formic acid, acetic acid, propionic acid, glycolic acid, fumaric acid, succinic acid, tartaric acid, ascorbic acid, salicylic acid, lactic acid, malic acid, methanesulfonic acid, p-toluenesulfonic acid and the like, but not limited thereto.

Among preferred compounds of the present invention are the compounds of Formula I wherein $R^1$ is an alkyl group having 1 to 3 carbon atoms or a methoxymethyl group, and $R^2$ is an alkyl group having 1 to 3 carbon atoms.

The compound of the present invention can be prepared, for example, in accordance with the following reaction scheme:

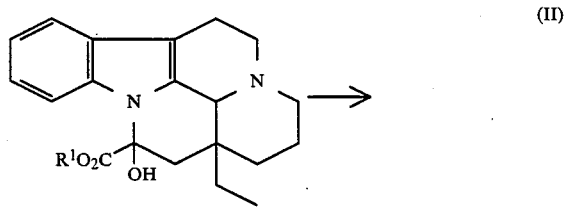

(II)

-continued

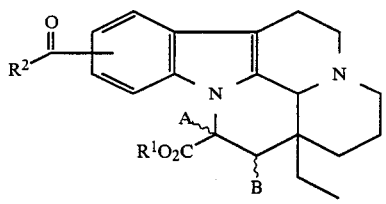

in which R¹, R², A and B are as defined above.

Namely, the known vincaminic acid derivatives of Formula II is subjected to a Friedel Crafts Reaction using an acylating agent having the group R²CO— (wherein R² is other than a hydrogen atom) in the presence of a Lewis acid to give the compound of Formula I wherein R² is other than a hydrogen atom. Alternatively, the use of dichloromethyl methyl ether in place of the acylating agent in the above reaction gives the compound of Formula I wherein R² is a hydrogen atom. The acylating agents used in the present invention are carboxylic acid halides or carboxylic acid anhydrides such as, for example, saturated aliphatic carboxylic acid halides (e.g., acetyl chloride, propionyl chloride, isovaleryl chloride, pivalyl chloride, capryl chloride, acetyl bromide and the like), saturated aliphatic carboxylic acid anhydrides (e.g., acetic anhydride, propionic anhydride, caproic anhydride, caprylic anhydride and the like), halogenated saturated aliphatic carboxylic acid halide (e.g., chloroacetyl chloride, chloropropionyl chloride, bromoacetyl chloride, fluoroacetyl chloride, chlorovaleryl bromide and the like), halogenated saturated aliphatic carboxylic acid anhydrides (e.g., chloropropionic anhydride, chlorovaleric anhydride, chlorocaproic anhydride, bromobutyric anhydride, bromopropionic anhydride, fluoroacetic anhydride and the like), benzoyl halide and benzoic anhydride. When R² is the cycloalkyl group, phenyl group, alkoxycarbonylalkyl group, alkenyl group, phenyl group substituted by the alkoxy groups or thienyl group, the corresponding acid halides or acid anhydrides can be used.

Examples of the Lewis acid are those used in the ordinary Friedel Crafts Reaction such as aluminium chloride, ferric chloride, tin tetrachloride, titanium tetrachloride and the like. Examples of the solvent are also those used in the ordinary Friedel Crafts Reaction such as, for example, methylene chloride, ethylene chloride, carbon disulfide, carbon tetrachloride, nitromethane, nitroethane, nitrobenzene and a mixture thereof.

The reaction time is from 10 minutes to 24 hours, and preferably from 30 minutes to 4 hours.

When carried out at 20° C. or higher, the Friedel Crafts Reaction gives mainly the compound of Formula I wherein A and B together form a valence bond. On the other hand, when carried out at a low temperature (−15° to 5° C.), the reaction gives mainly the compound of Formula I wherein A is a hydroxyl group B is a hydrogen atom.

The compound of Formula I thus obtained can be isolated by column chromatography or recrystallization.

Alternatively, the compound of the present invention can be also prepared by the following method. Namely, the compound of Formula I wherein R¹ is other than a hydrogen atom is subjected to ester exchange reaction under an acid catalyst or a base catalyst to give a compound of Formula I wherein R¹ is different group within the scope.

Furthermore, the compound of Formula I wherein R¹ is a hydrogen atom is reacted with a halide of R¹X (wherein R¹ is other than a hydrogen atom and X is a halogen atom) in the presence of a base (e.g., sodium hydroxide, potassium carbonate, sodium hydride, potassium hydride and the like) to give the compound of Formula I wherein R¹ is other than a hydrogen atom.

The compound of the present invention have excellent preventive and therapeutic effects on diseases caused by the cerebovascular injuries such as cerebral infaction, cerebral stroke, arteriosclerosis and senile dementia. For these purposes, these compounds can be administered orally or parenterally in a conventional dosage forms such as tablets, powders, granules, capsules, solutions, emulsions, suspensions, injectional solutions and the like, each of which can be prepared in accordance with ordinary pharmaceutical practices.

When the compound of the present invention is used as a therapeutic agent of the cerebral infaction, the dose depends on the age, body weight, response of the patient, route of administration or time of administration, but usually it may be from 1 to 100 mg per day.

The present invention is illustrated by the following examples and experiments in more detail.

EXAMPLE 1

Methyl 10-acetylapovincaminate, methyl 11-acetylapovincaminate and methyl 12-acetylapovincaminate To 50 ml of methylene chloride was suspended 3.33 g of aluminium chloride under a nitrogen atmosphere, and 1.96 ml of acetyl chloride was added to the suspension. The mixture was stirred for 30 minutes, and 1.77 g of vincamine was added at room temperature followed by stirring at 40° C. for 30 minutes.

The cooled reaction solution was mixed with 50 ml of a saturated aqueous potassium sodium tartrate solution, 50 ml of 10% sodium carbonate and 50 ml of ice water, and the mixture was extracted 5 times with 50 ml of methylene chloride. The organic layer was dried over anhydrous sodium sulfate, and concentrated under reduced pressure.

The residue was applied to silica gel column chromatography (Wako-gel C-200, 50 g) and eluted with ethyl ether:hexane (4:1). Two groups of fractions having ultraviolet absorption at 254 nm were each collected by identifying by silica gel thin layer chromatography. The fractions which were later eluted were concentrated, a small amount of ethyl ether was added, and the mixture was allowed to stand. The crystals which formed were recrystallized from methanol to give 1. g of methyl 10-acetylapovincaminate as colorless crystals.

m.p. 156°–157° C.

NMR (CDCl₃, 200 MHz) δ (ppm): 8.12(1H, d, J=2 Hz), 7.81(1H, dd, J=8 Hz, 2 Hz), 7.26(1H, d, J=8 Hz), 6.27(1H, s), 4.ll(1H, s), 3.96(3H, s), 3.35(1H, dd, J=14 Hz, 6 Hz), 2.65(3H, s), 1.02(3H, t, J=7 Hz), 0.96(1H, dd, J=13 Hz, 4 Hz)

The fractions which were earlier eluted by silica gel chromatography were concentrated, a small amount of ethyl ether was added, and the mixture was allowed to stand. The crystals which formed were recrystallized from methanol to give 127 mg of methyl 12-acetylapovincaminate as colorless crystals.

m.p. 211°–212° C.

NMR (CDCl$_3$, 200 MHz) δ (ppm): 7.63(1H, d, J=8 Hz), 7.58(1H, d, J=8 Hz), 7.13(1H, t, J=8 Hz), 6.37(1H, s), 3.95(1H, s), 3.78(3H, s), 2.61(3H, s), 1.01(3H, t, J=8 Hz)

The solution obtained after elution of methyl 12-acetylapovincaminate was fractionated by silica gel thin layer chromatography (20 cm×20 cm×4 pieces, methanol:chloroform=3:97) and eluted with ethyl acetate. The eluate was concentrated to give 152 mg of methyl 11-acetylapovincaminate as colorless powders.

NMR (CDCl$_3$, 200 MHz) δ (ppm): 7.93(1H, d, J=2 Hz), 7.75(1H, dd, J=8 Hz, 2 Hz), 7.48(1H, d, J=8 Hz), 6.26(1H, s), 4.14(1H, s), 3.98(3H, s), 2.63(3H, s), 1.03(3H, t, J=7 Hz), 0.93(1H, dd, J=13 Hz, 4 Hz)

EXAMPLE 2

Methyl 10-chloroacetylapovincaminate, and methyl 11-chloroacetylapovincaminate

In 50 ml of methylene chloride was suspended 3.33 g of aluminium chloride under a nitrogen atmopshere, and 2 ml of chloroacetyl chloride was added to the suspension. The mixture was stirred for 30 minutes, and 1.77 g of vincamine was added at room temperature followed by stirring at 40° C. for 30 minutes.

The cooled reaction solution was mixed with 50 ml of a saturated aqueous potassium sodium tartrate solution, 50 ml of 10% sodium carbonate and 50 ml of ice water, and the mixture was extracted 5 times with 50 ml of methylene chloride. The organic layer was dried over anhydrous sodium sulfate, and concentrated under reduced pressure.

The residue was applied to silica gel column chromatography (Wako-gel C-200, 50 g) and eluted with ethyl ether:hexane (4:1). Two groups of fractions having ultraviolet absorption at 254 nm were each collected by identifying by silica gel thin layer chromatography. The fractions which were eluted later were concentrated, a small amount of ethyl ether was added, the mixture was allowed to stand. The crystals which formed were recrystallized from methanol to give 1.0 g of methyl 10-chloroacetylapovincaminate as colorless crystals.

NMR (CDCl$_3$, 200 MHz) δ (ppm): 8.13(1H, d, J=2 Hz), 7.79(1H, dd, J=9 Hz, 2 Hz), 7.29(1H, d, J=9 Hz), 6.31(1H, s), 4.79(2H, s), 4.12(1H, s), 3.97(3H, s), 1.03(3H, t, J=7 Hz), 0.95(1H, dd, J=12 Hz, 4 Hz)

The fractions which were earlier eluted with silica gel chromatography were concentrated, and fractionated by silica gel thin layer chromatography (20 cm×20 cm×4 pieces, 3% methanol/chloroform) to give 300 mg of methyl 11-chloroacetylapovincaminate.

NMR (CDCl$_3$, 200 MHz), δ (ppm): 7.97(1H, d, J=2 Hz), 7.72(1H, dd, J=8 Hz, 2 Hz), 7.51(1H, d, J=8 Hz), 6.31(1H, s), 4.79(2H, s), 4.12(1H, s), 3.99(3H, s), 1.03(3H, t, J=7 Hz), 0.95(1H, dd, J=12 Hz, 4 Hz)

EXAMPLE 3

Methyl 10-formylapovincaminate hydrochloride and methyl 11-formylapovincaminate hydrochloride In a mixture of 50 ml of nitromethane and 200 ml of methylene chloride was suspended 26.4 g of aluminium chloride, and stirring was continued for about 1 hour until the suspension became clear in color. To the reaction solution was added 13.2 g of vincamine, and the mixture was stirred for 30 minutes. 18 ml of dichloromethyl methyl ether was added, and the mixture was stirred for 30 minutes. The reaction solution was poured into 200 ml of ice, and then 100 ml of a saturated aqueous potassium sodium tartrate solution and 100 ml of saturated aqueous sodium carbonate solution were added. The mixture was extracted 3 times with 200 ml of methylene chloride, and the extracts were combined and concentrated.

The residue was applied to silica gel column chromatography (Wako-gel C-200, 300 g) and eluted with ethyl ether:hexane (4:1). Two groups of fractions having ultraviolet absorption at 254 nm were each collected by identifying by silica gel thin layer chromatography.

The fractions which were earlier eluted were concentrated under reduced pressure, the residue was further dissolved in 30 ml of ethyl ether, and then hydrochloric acid gas was introduced. The crystals which formed were collected and recrystallized from methanolethyl ether to give 1.8 g of methyl 11-formylapovincaminate hydrochloride as colorless crystals.

m.p. 200°–205° C.

NMR (DMSO-d$_6$, 200 MHz) δ (ppm): 12.05(1H, br, s), 10.02(1H, s), 7.88(1H, d, J=1Hz), 7.79(1H, d, J=9 Hz), 7.71(1H, d, J=9 Hz, 1 Hz), 6.33(1H, s), 5.12(1H, s), 3.95(3H, s), 1.00(3H, t, J=7 Hz)

The fractions which were later eluted were treated similarly to give 7 g of methyl 10-formylapovincaminate hydrochloride.

m.p. 205°–210° C.

NMR (DMSO-d$_6$, 200 MHz) δ (ppm): 12.10(1H, br, s), 10.04(1H, s), 8.22(1H, d, J=1Hz), 7.75(1H, dd, J=9 Hz, 1Hz), 7.45(1H, d, J=9 Hz), 6.34(1H, s), 5.06(1H, s), 3.94(3H, s), 0.99(3H, t, J=7 Hz)

EXAMPLE 4

Methyl 10-(3,4,5-trimethoxybenzoyl)apovincaminate

In a mixture of 5 ml of nitromethane and 25 ml of methylene chloride was suspended 3.3 g of aluminium chloride, and stirring was continued for about 1 hour until the suspension became clear in color. To the reaction solution was added 1.77 g of vincamine, and the mixture was stirred for 30 minutes. 3.45 g of 3,4,5-trimethoxybenzoyl chloride was added, and the mixture was stirred for 30 minutes. To the reaction solution were added 50 ml of a saturated aqueous potassium sodium tartrate solution and 50 ml of a saturated aqueous sodium carbonate solution. The mixture was extracted twice with 100 ml of methylene chloride, and the extracts were combined and concentrated.

The residue was applied to silica gel column chromatography (Wako-gel C-200, 100 g) and eluted with ethyl ether. The fractions having ultraviolet absorption at 254 nm were collected by identifying by silica gel thin layer chromatography and concentrated under reduced pressure. The residue was recrystallized from ethyl ether to give 280 mg of methyl 10-(3,4,5-trimethoxybenzoyl)apovincaminate.

m.p. 210°–212° C.

NMR (DMSO-d$_6$, 200 MHz) δ (ppm): 8.01(1H, d, J=1Hz), 7.68(1H, dd, J=9 Hz, 1 Hz), 7.31(1H, d, J=9 Hz), 7.10(2H, s), 6.30(1H, s), 4.14(1H, s), 3.97(3H, s), 3.94(3H, s), 3.88(6H, s), 1.03(3H, t, J=7 Hz)

EXAMPLE 5

Methyl 10-propionylapoapovincaminate hydrochloride

In a mixture of 5 ml of nitromethane and 25 ml of methylene chloride was suspended 6.66 g of aluminium chloride, 4.6 g of propionyl chloride was added, and stirring was continued for about 1 hour until the mixture became clear in color. To the reaction solution was added 3.54 g of vincamine, and the mixture was stirred at 35° to 40° C. for one hour. To the reaction solution were added 50 ml of a saturated aqueous potassium sodium tartrate solution and 50 ml of a saturated aqueous sodium carbonate solution. The mixture was extracted twice with 100 ml of methylene chloride, and the extracts were combined and concentrated.

The residue was applied to silica gel column chromatography (Wako-gel C-200, 200 g) and eluted with ethyl ether. The fractions having ultraviolet absorption at 254 nm were collected by identifying by silica gel thin layer chromatography and concentrated under reduced pressure. The residue was further dissolved in 30 ml of ethyl ether, and hydrochloric acid gas was introduced. The crystals which formed were recrystallized from methanol-ethyl ether to give 1.81 g of methyl 10-propionylapoapovincaminate hydrochloride.

m.p. 193°–196° C.

NMR (DMSO-$d_6$, 200 MHz) δ (ppm): 12.05(1H, br, s), 8.27(1H, d, J=1 Hz), 7.84(1H, d, J=9 Hz, 1Hz), 7.36(1H, d, J=9 Hz), 6.30(1H, s), 5.05(1H, br, s), 3.93(3H, s), 12(3H, t, J=7 Hz), 0.99(3H, t, J=7 Hz)

Following the procedure of Example 5, the following compounds were obtained.

Methyl 10-decanoylapovincaminate hydrochloride m.p. 169°–172° C.

NMR (DMSO-$d_6$, 200 MHz) δ (ppm): 12.00(1H, br, s), 8.27(1H, d, J=1 Hz), 7.81(1H, dd, J=9 Hz, 1 Hz), 7.35(1H, d, J=9 Hz), 6.29(1H, s), 5.05(1H, s), 3.94(3H, s), 1.30(12H, br, s), 0.99(3H, t, J=7 Hz), 0.86(3H, t, J=7 Hz)

Methyl 10-[3-(ethoxycarbonyl)propionyl]apovincaminate hydrochloride m.p. 155°–160° C.

NMR (DMSO-$d_6$, 200 MHz) δ (ppm): 11.80(1H, br, s), 8.31(1H, d, J=1 Hz), 7.84(1H, dd, J=9 Hz, 1 Hz), 7.37(1H, d, J=9 Hz), 6.30(1H, s), 5.08(1H, s), 4.06(2H, q, J=7 Hz), 3.94(3H, s), 3.38(2H, t, J=4 Hz), 2.67(2H, t, J=4 Hz), 1.18(3H, t, J=7 Hz), 0.99(3H, t, J=7 Hz)

Methyl 10-(3-chlorobutyryl)apovincaminate hydrochloride m.p. 175°–180° C.

Methyl 10-benzoylapovincaminate hydrochloride m.p. 168°–173° C.

NMR (DMSO-$d_6$, 200 MHz) δ (ppm): 12.10(1H, br, s), 8.08(1H, d, J=1 Hz), 7.43(1H, d, J=9 Hz), 6.31(1H, s), 5.07(1H, s), 3.95(3H, s), 1.00(3H, t, J=7 Hz)

Methyl 10-(2-thenoyl)apovincaminate hydrochloride m.p. 175°–180° C.

NMR (DMSO-$d_6$, 200 MHz) δ (ppm): 11.80(1H, br, s), 8.14(1H, d, J=1 Hz), 8.12(1H, dd, J=5 Hz, 1 Hz), 7.81(1H, dd, J=3 Hz, 1 Hz), 7.74(1H, dd, J=9 Hz, 1 Hz), 7.44(1H, d, J=9 Hz), 7.32(1H, dd, J=5 Hz, 3 Hz), 6.31(1H, s), 5.10(1H, s), 3.95(3H, s), 1.00(3H, t, J=7 Hz)

Methyl 10-(3,3-dimethylacroyl)apovincaminate hydrochloride m.p. 195°–200° C.

NMR (DMSO-$d_6$, 200 MHz) δ (ppm): 11.70(1H, br, s), 8.23(1H, d, J=1 Hz), 7.84(1H, dd, J=9 Hz, 1 Hz), 7.36(1H, d, J=9 Hz), 7.02(1H, s), 6.30(1H, s), 5.10(1H, s), 3.94(3H, s), 2.18(3H, s), 2.02(3H, s), 0.99(3H, t, J=7 Hz)

Methyl 10-cyclohexanecarbonylapovincaminate hydrochloride m.p. 185°–188° C.

NMR (DMSO-$d_6$, 200 MHz) δ (ppm): 11.70(1H, br, s), 8.26(1H, d, J=1 Hz), 7.82(1H, dd, J=9 Hz, 1 Hz), 7.35(1H, d, J=9 Hz), 6.29(1H, s), 5.06(1H, s), 3.93(3H, s), 0.99(3H, t, J=7 Hz)

Methyl 10-isobutyrylapovincaminate hydrochloride m.p. 170°–175° C.

NMR (DMSO-$d_6$ 200 MHz) δ (ppm): 11.80(1H, br, s), 8.29(1H, d, J=1 Hz), 7.85(1H, dd, J=9 Hz, 2 Hz), 7.37(1H, d, J=9 Hz), 6.30(1H, s), 5.07(1H, br, s), 3.94(3H, s), 1.15(3H, d, J=7 Hz), 1.14(3H, d, J=7 Hz), 0.99(3H, t, J=7 Hz)

Methyl 10-n-butyrylapovincaminate hydrochloride m.p. 193°–196° C. NMR (DMSO-$d_6$, 200 MHz) δ (ppm): 11.80(1H, br, s), 8.28(1H, d, J=1 Hz), 7.83(1H, dd, J=9 Hz, 1 Hz), 7.36(1H, d, J=9 Hz), 6.30(1H, s), 5.07(1H, s), 3.93(3H, s), 3.06(2H, t, J=7 Hz), 1.68(2H, dt, J=7 Hz, 7 Hz), 1.02(3H, t, J=7 Hz), 0.96(3H, t, J=7 Hz)

Methyl 11-acetylapovincaminate hydrochloride m.p. 185°–190° C.

NMR (DMSO-$d_6$, 200 MHz) κ (ppm): 11.68(1H, br, s), 7.91(1H, d, J=1 Hz), 7.81(1H, d, J=9 Hz, 1 Hz), 7.70(1H, d, J=9 Hz), 6.32(1H, s), 5.11(1H, s), 3.94(3H, s), 2.61(3H, s), 1.01(3H, t, J=7 Hz)

Methyl 10-acetylapovincaminate hydrochloride m.p. 206°–208° C.

NMR (DMSO-$d_6$, 200 MHz) Δ (ppm): 11.96(1H, br, s), 8.27(1H, d, J=1 Hz), 7.83(1H, d, J=9 Hz, 1 Hz), 7.36(1H, dd, J=9 Hz, 1 Hz), 6.30(1H, s), 5.06(1H, s), 3.93(3H, s), 2.63(3H, s), 1.02(3H, t, J=7 Hz)

Methyl 10-(4-chlorobutyryl)apovincaminate hydrochloride

NMR (DMSO-$d_6$, 200 MHz) δ (ppm): 11.70(1H, br, s), 8.29(1H, d, J=1 Hz), 7.83(1H, dd, J=9 Hz, 1 Hz), 7.37(1H, d, J=9 Hz), 6.30(1H, s), 5.08(1H, s), 3.94(3H, s), 3.75(2H, t, J=7 Hz), 3.25(2H, t, J=7 Hz), 2.11(2H, t, J=7 Hz), 1.00(3H, t, J=7 Hz)

Methyl 10-(t-butylacetyl)apovincaminate hydrochloride m.p. 168°–172° C.

NMR (DMSO-$d_6$, 200 MHz) δ (ppm): 11.95(1H, br, s), 8.28(1H, d, J=1 Hz), 7.84(1H, dd, J=9 Hz, 1 Hz), 7.34(1H, d, J=9 Hz), 6.29(1H, s), 5.06(1H, s), 3.93(3H, s), 3.39(1H, s), 1 03(9H, s), 0.99(3H, t, J=7 Hz)

Methyl 10-isovalerylapovincaminate hydrochloride m.p. 180°–182° C.

NMR (DMSO-$d_6$, 200 MHz) δ (ppm): 12.01(1H, br, s), 8.27(1H, d, J=1 Hz), 7.83(1H, dd, J=9 Hz, 1 Hz), 7.35(1H, d, J=9 Hz), 6.30(1H, s), 5.06(1H, s), 3.93(3H, s), 2.83(2H, d, J=7 Hz), 1.01(3H, t, J=6 Hz), 0.95(6H, d, J=6 Hz)

EXAMPLE 6

Ethyl 10-acetylapovincaminate hydrochloride

To a solution of 1 g of methyl 10-acetylapovincaminate hydrochloride in 20 ml of ethanol was added 2 ml of conc. hydrochloride acid, and the mixture was refluxed under heating for 24 hours. The reaction solution was adjusted to pH 7 with a saturated aqueous potassium carbonate solution and extracted twice with 50 ml of methylene chloride. The organic layer was dried over anhydrous sodium sulfate and concentrated under reduced pressure. The residue was dissolved in 30 ml of ethyl ether, and hydrochloric acid gas was introduced. The crystals which formed were collected and recrystallized from methanol - ethyl ether to give 1 g of ethyl 10-acetylapovincaminate hydrochloride.

m.p. 217°–220° C.

NMR (DMSO-$d_6$, 200 MHz) δ (ppm): 12.00(1H, br, s), 8.28(1H, d, J=1 Hz), 7.84(1H, dd, J=9 Hz), 7.36(1H, d, J=9 Hz), 6.25(1H, s), 5.07(1H, s), 4.40(1H, q, J=7 Hz), 2.64(1H, s), 1.32(3H, t, J=7 Hz), 0.99(3H, t, J=7 Hz)

Following the procedure of Example 6, the following compounds were obtained.

Ethyl 10-propionylapovincaminate hydrochloride m.p. 191°–194° C.

NMR (DMSO-$d_6$, 200 MHz) δ (ppm): 12.10(1H, br, s), 8.28(1H, d, J=1 Hz), 7.84(1H, dd, J=9 Hz, 1 Hz), 7.35(1H, d, J=9 Hz), 6.28(1H, s), 5.08(1H, s), 4.40(2H, q, J=7 Hz), 3.20(2H, q, J=7 Hz), 1.32(3H, t, J=7 Hz), 1.13(3H, t, J=7 Hz), 0.99(3H, t, J=7 Hz)

Ethyl 10-isobutyrylapovincaminate hydrochloride m.p. 181°–185° C.

NMR (DMSO-$d_6$, 200 MHZ) δ (ppm): 11.96(1H, br, s), 8.29(1H, d, J=1 Hz), 7.83(1H, dd, J=9 Hz, 1 Hz), 7.36(1H, d, J=9 Hz), 6.28(1H, s), 5.07(1H, br, s), 4.40(2H, q, J=7 Hz), 1.34(3H, t, J=7 Hz), 1.14(6H, br, d, J=7 Hz), 0.99(3H, t, J=7 Hz)

n-Propyl 10-acetylapovincaminate hydrochloride m.p. 213°–215° C.

NMR (DMSO-$d_6$, 200 MHz) δ (ppm): 12.15(1H, br, s), 8.27(1H, d, J=1 Hz), 7.83(1H, dd, J=9 Hz, 1 Hz), 7.36(1H, d, J=9 Hz), 7.28(1H, s), 5.06(1H, br, s), 4.32(2H, t, J=7 Hz), 2.63(3H, s), 0.99(3H, t, J=7 Hz), 0.92(3H, t, J=7 Hz)

Isopropyl 10-acetylapovincaminate hydrochloride

NMR (DMSO-$d_6$, 200 MHz) δ (ppm): 12.22(1H, br, s), 8.27(1H, d, J=1 Hz), 7.85(1H, dd, J=9 Hz), 7.33(1H, d, J=9 Hz), 6.23(1H, s), 5.05(1H, s), 2.64(3H, s), 1.37(3H, d, J=7 Hz), 1.34(3H, t, J=7 Hz), 0.99(3H, t, J=7 Hz)

n-Butyl 10-acetylapovincaminate hydrochloride m.p. 220°–222° C.

NMR (DMSO-$d_6$, 200 MHz) δ (ppm): 11.90(1H, br, s), 8.29(1H, d, J=1 Hz), 7.85(1H, d, J=9 Hz, 1 Hz), 7.35(1H, dd, J=9 Hz), 6.29(1H, s), 5.10(1H, s), 4.38(3H, s), 2.65(3H, s), 1.01(3H, t, J=7 Hz), 0.95(3H, t, J=9 Hz)

n-Pentyl 10-acetylapovincaminate m.p. 221°–223° C.

NMR (DMSO-$d_6$, 200 MHz) δ (ppm): 8.28(1H, d, J=1 Hz), 7.83(1H, dd, J=9 Hz, 1 Hz), 7.35(1H, d, J=9 Hz), 6.27(1H, s), 5.08(1H, s), 4.37(2H, t, J=7 Hz), 3.40(3H, s), 0.99(3H, t, J=7 Hz), 0.89(3H, t, J=7 Hz)

n-Hexyl 10-acetylapovincaminate m.p. 203°–205° C.

NMR (DMSO-$d_6$, 200 MHz) δ (ppm): 8.17(1H, d, J=1 Hz), 7.91(1H, dd, J=9 Hz, 1 Hz), 7.35(1H, d, J=9 Hz), 6.26(1H, s), 4.68(1H, s), 2.68(3H, s), 1.13(3H, t, J=7 Hz), 0.90(3H, t, J=7 Hz)

EXAMPLE 7

10-acetylapovincaminic acid

In a mixture of 50 ml of acetone, 20 ml of water and 20 ml of methanol were dissolved 2.475 g of methyl 10-acetylapovincaminate and 2.23 g of potassium hydroxide, and the solution was stirred at room temperature for 3 hours. The reaction solution was concentrated under educed pressure and adjusted to pH 7 with 1N-hydrochloric acid. The crystals which formed were collected, washed with ethyl ether and dried to give 900 mg of 10-acetylapovincaminic acid.

NMR (DMSO-$d_6$, 200 MHz) δ ppm): 8.27(1H, d, J=1 Hz), 7.84(1H, dd, J=9 Hz, 1 Hz), 7.43(1H, d, J=9 Hz), 6.27(1H, s), 5.02(1H, br, s), 2.63(3H, s), 0.99(3H, t, J=7 Hz)

EXAMPLE 8

11-Acetylvincamine

To a suspension of 940 mg of aluminum chloride in 25 ml of methylene chloride was added 0.6 ml of acetyl chloride, and stirring was continued for about 1 hour until the mixture became clear in color. The reaction solution was cooled to 0° C. on ice-bath, and 500 mg of vincamine was added. After removing ice-bath, the mixture was stirred for 1 hour. To the reaction solution were added 10 ml of a saturated aqueous potassium sodium tartrate solution and 10 ml of a saturated aqueous potassium carbonate solution, and the mixture was extracted twice with 30 ml of methylene chloride. The extracts were combined, dried over anhydrous sodium sulfate and concentrated under reduced pressure.

The residue was applied to silica gel column chromatography (Wako-gel C-200, 30 g) and eluted with ethyl ether:hexane (4:1). The first eluted fractions having ultraviolet absorption at 254 nm were collected by identifying by silica gel thin layer chromatography. The fractions were concentrated under reduced pressure, the residue was further applied to silica gel column chromatography (Wako-gel C-200, 50 g) and eluted with 1% methanol - chloroform. The second eluted fractions having ultraviolet absorption at 254 nm were concentrated and recrystallized from methanol to give 150 mg of 11-acetylvincamine.

NMR (DMSO-$d_6$, 200 MHz) δ (ppm): 7.76(1H, d, J=1 Hz), 7.68(1H, dd, J=9 Hz, 1 Hz), 7.47(1H, d, J=9 Hz), 3.80(1H, s), 2.55(3H, s), 0.83(3H, t, J=7 Hz)

EXAMPLE 9

Methoxymethyl 10-acetylapovincaminate

In a suspension of 1 g of 10-acetylapovincaminic acid and 400 mg of potassium carbonate in a mixture of dimethylformamide-acetone (10 ml - 10 ml) was added 0.3 ml of chloromethyl methyl ether, and then the mixture was stirred at room temperature for 6 hours. The reaction mixture was poured into 100 ml of water and extracted twice with 100 ml of ethyl acetate. The extract was dried and concentrated, and the residue was applied to silica gel column chromatography (Wako-gel C-200, 50 g) and eluted with ethyl ether. The fractions having ultraviolet absorption at 254 nm were collected and concentrated under the mixture was allowed to stand.

The crystals which were filtered to give 600 mg of methoxymethyl 10-acetylapovincaminate.

m.p. 117°–119° C.

NMR (DMSO-d$_6$, 200 MHz) δ (ppm): 8.13(1H, d, J=1 Hz), 7.81(1H, dd, J=9 Hz, 1 Hz), 7.32(1H, d, J=9 Hz), 6.36(1H, s), 5.51(2H, s), 4.25(1H, s), 3.58(3H, s), 2.67(3H, s), 1.03(3H, t, J=7 Hz)

Experiment 1: Effect on increase of survival time by potassium cyanate

The drugs (methyl 10-acetylapovincaminate and ethyl 10-propionylapovincamine hydrochloride of the present invention and (+)-ethyl apovincaminate and 11-bromovincamine as the control drugs) were each suspended in gum arabic and administered orally in a given dose to male ICR strain mice (each group consists of 8 animals). After 30 minutes, potassium cyanate (5 mg/kg) was injected in the tail vein to measure the time until the respiration ceased. The dose at which the survival time of the mice treated with the drug is increased at a level of statistical significance compared with that of the group treated with physiological saline (statistical treatment was performed by means of the Dunnet method after dispersion analysis: p<0.01) is expressed as the minimum effective dose.

The data are shown in Table 1.

TABLE 1

| Compound | Minimum effective dose (mg/kg) |
|---|---|
| (+)-ethyl apovincaminate | 100 |
| 11-bromovincamine | ≧100 |
| methyl 1-acetylapovincaminate | 10 |
| ethyl 10-propionylapovincaminate hydrochloride | 10 |

EXPERIMENT 2: ANTIHYPOXIC EFFECT TEST

The test was carried out according to the method as described by Rosner et al. in Arch. Int. Pharmacodyn. Ther., vol. 194, pages 375–380 (1971), and 8 male Wister strain rats, weighing 280–390 g, were used for each group. Rats were anesthetized with ether ether, administered intravenously 0.05 ml/kg of 2% aqueous gallamine triethiodide solution to stop the respiration. The rats were set up an arterial catheter and fixed with a brain stereotaxic apparatus under artificial respiration. The cortical brain waves were recorded bilateral from the motor area. The body temperature was kept at 37°–39° C. during the recording. After one hour, the drug was dissolved in 10% aqueous ascorbic acid solution and administered intravenously in an amount of 1 ml/1 kg body weight. After 10 minutes, the artificial respiration was suspended, and the time until the brain waves were disappeared was measured.

When the time until the brain waves were disappeared in the animals treated with the drug is increased at a level of statistical significance compared with that of the control group administered an aqueous ascorbic acid solution only (statistical treatment was performed by means of the Dunnet method after dispersion analysis: p<0.01), the animals were considered as protected from the hydroxemia conditions.

The test results were expressed as the minimum effective dose to significantly increase the time until the brain waves was disappeared, and shown in Table 2.

It was apperant from the results that methyl 10-acetylapovincaminate and ethyl 10-propionylapovincaminate are 3 to 10 times as active as (+)-ethyl apovincaminate and 11-bromovincaminic acid used as the control drugs in the brain protect action to hypoxia.

TABLE 2

| Compound | Minimum effective dose (mg/kg) |
|---|---|
| 11-bromovincamine | 20 |
| (+)-ethyl apovincaminate | 10 |
| methyl 10-acetylapovincaminate | 3 |
| ethyl 10-provionylapovincaminate | 2 |

EXAMPLE 3: PERIPHERAL VASODILATING ACTIVITY TEST

Peripheral vasodilating activity was examined using dogs anesthetized with 5% sodium pentobarbital (30 mg/kg), the drugs (methyl 10-acetylapovincaminate hydrochloride and ethyl 10-propionylapovincamin hydrochloride) were each administered intravenously in amount of 3 mg/kg body weight. The increase of the blood flow measured in the femoral vein were compared with the blood flow of the pretreated dogs, and expressed as percent. (+)-Ethylapovincaminate and 11-bromovincaminate were used as the comparative drugs.

The results were shown in Table 3.

TABLE 3

| Compound | Increase of blood flow (%) |
|---|---|
| (+)-ethyl apovincaminate | 70 |
| 11-bromovincamine | 80 |
| methyl 10-acetylapovincaminate hydrochloride | 180 |
| ethyl 10-propionylapovincaminate hydrochloride | 220 |

What is claimed is:

1. Vincaminic acid derivatives represented by the formula

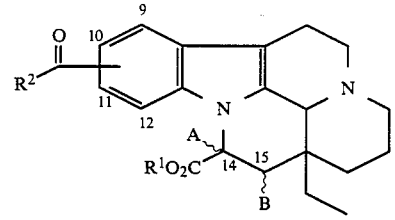

wherein R$^1$ is a hydrogen atom, an alkyl group having 1 to 8 carbon atoms or an alkoxyalkyl group having 2 to 6 carbon atoms, R$^2$ is a hydrogen atom, an alkyl group having 1 to 10 carbon atoms, a halogenated alkyl group having 1 to 5 carbon atoms, a cycloalkyl group having 3 to 6 carbon atoms, an alkoxycarbonylalkyl group having 3 to 8 carbon atoms, an alkenyl group having 2 to 4 carbon atoms, a phenyl group, a phenyl group substituted by alkoxy groups each having 1 or 2 carbon atoms or a thienyl group, A is a hydroxyl group, B is a hydrogen atom, or A and B together form a valence bond, and the acid addition salts thereof.

2. The vincaminic acid derivative according to claim 1 wherein R$^1$ is an alkyl group having 1 to 3 carbon atoms or a methoxymethyl group, and R$^2$ is an alkyl group having 1 to 3 carbon atoms.

* * * * *

UNITED STATES PATENT AND TRADEMARK OFFICE
CERTIFICATE OF CORRECTION

PATENT NO. : 4,883,876

DATED : November 28, 1989

INVENTOR(S) : NAKATSUKA et al

It is certified that error appears in the above-identified patent and that said Letters Patent is hereby corrected as shown below:

<u>IN THE ABSTRACT:</u>

Line 11, "hydroxy" should read --hydroxyl--.

Col. 4, line 54, "1." should read --1.0--.

Col. 7, line 22, "12" should read --1.12--.

Col. 8, line 12, "(DMSO-d$_6$200 MHz)" should read --(DMSO-d$_6$,200 MHz)--;

line 28, "𝘒" should read --$\delta$--;

line 35, "Δ" should read --$\delta$--; and line 55, "1 03" should read --1.03--.

Col. 9, line 31, "6" should read --$\delta$--;

between lines 45 and 46 insert --m.p. 228 - 232°C--.

Col. 10, line 18, "6 ppm" should read --$\delta$ (ppm--;

line 68, after "under" insert --reduced pressure, a small amount of ethyl ether was added, and--.

UNITED STATES PATENT AND TRADEMARK OFFICE
CERTIFICATE OF CORRECTION

PATENT NO. : 4,883,876

DATED : November 28, 1989

INVENTOR(S) : NAKATSUKA et al

It is certified that error appears in the above-identified patent and that said Letters Patent is hereby corrected as shown below:

Col. 11, line 1, after "which" insert --formed--.

Signed and Sealed this

Second Day of October, 1990

Attest:

HARRY F. MANBECK, JR.

*Attesting Officer*     *Commissioner of Patents and Trademarks*